(12) United States Patent
Lloyd

(10) Patent No.: US 7,091,355 B2
(45) Date of Patent: Aug. 15, 2006

(54) CHIRAL SCAFFOLDS AND THEIR PREPARATION

(75) Inventor: Richard Lloyd, Cambridge (GB)

(73) Assignee: Dow Global Technologies Inc., Midland, MI (US)

( * ) Notice: Subject to any disclaimer, the term of this patent is extended or adjusted under 35 U.S.C. 154(b) by 0 days.

(21) Appl. No.: 10/433,989

(22) PCT Filed: Dec. 21, 2001

(86) PCT No.: PCT/GB01/05735

§ 371 (c)(1),
(2), (4) Date: Jun. 10, 2003

(87) PCT Pub. No.: WO02/053536

PCT Pub. Date: Jul. 11, 2002

(65) Prior Publication Data

US 2004/0063609 A1    Apr. 1, 2004

(30) Foreign Application Priority Data

Dec. 29, 2000  (GB) ................... 0031808.9
Dec. 29, 2000  (GB) ................... 0031810.5

(51) Int. Cl.
C07D 211/36    (2006.01)
(52) U.S. Cl. .................................... 546/242
(58) Field of Classification Search ........ 546/242
See application file for complete search history.

(56) References Cited

U.S. PATENT DOCUMENTS 3,852,283 A * 12/1974 Dolfini et al. ............ 540/228

FOREIGN PATENT DOCUMENTS

EP    0614986    9/1994

OTHER PUBLICATIONS

Nicolaou et al., J. Am. Chem. Soc., 1993, 115, 4419-4420.
Ornstein et al., J. Med. Chem., 1989, 32, 827-833.
Okamoto et al., Biochem. Biophys. Res. Commun., 1981, 101, 440-446.
Bruce et al., Tetrahedron, 1992, 46, 10191-10200.
Copeland et al., Biochem. Biophys. Res. Commun., 1990, 169, 310-314.
Couty, Amino Acids, 1999, 16, 297-320.
Hays et al., J. Org. Chem., 1990, 56, 4084-4086.
Beaulieu et al., J. Org. Chem., 1997, 62, 3440-3448.
Skiles et al., Bioorg. Med. Chem. Lett., 1996, 6, 963-966.
Golubevetal Tetrahedron Lett, 1995 36, 2037-2440.
Bousquet et al., Tetrahedron, 1997, 46, 15671-15680.
Di Nardo and Varela, J. Org. Chem., 1999, 64, 6119-6125.
Nin et al., Tetrahedron, 1993, 42, 9459-9464.
Pellicciari et al., Med. Chem. Res., 1992, 2, 491-496.
Wang et al., J. Org. Chem., 1998, 63, 4850-3.
Hiroya et al., Synthesis, 1995, 379-81.
Mulzer et al., Liebigs Ann. Chem., 1992, 1131-5.
Esch, et al., Tetrahedron, 1991, 47, 4063-4076.
Golubev, Tetrahedron Letters, vol. 42, p. 7941-7944, 2001.

* cited by examiner

Primary Examiner—D. Margaret Seaman

(57) ABSTRACT

A crystalline salt according to formula (1): or the opposite enantiomer thereof, wherein $X^+$ is a cation. Such salts are useful in preparing chiral scaffolds, in particular of formulae (a)–(d)

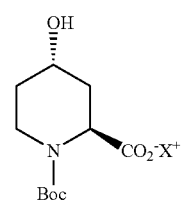

(1)

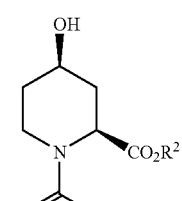

(a)

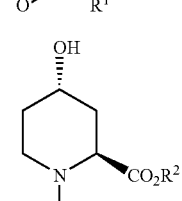

(b)

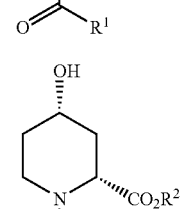

(c)

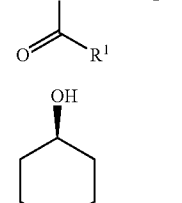

(d)

24 Claims, No Drawings

CHIRAL SCAFFOLDS AND THEIR PREPARATION

FIELD OF THE INVENTION

This invention relates to chiral scaffolds, to their preparation and also to novel chemical intermediates useful in the synthesis of such scaffolds; the scaffolds can be used for the preparation of information-rich single enantiomer compound libraries.

BACKGROUND OF THE INVENTION

Drug discovery may utilise, for screening, a library in which individual compounds are single isomers. This generates 3-dimensional information that can be enhanced by applying computational methods for lead optimisation. In order to prepare single isomer libraries, the appropriate chiral scaffold precursors should be in isomerically pure form, in which relative and absolute configuration is defined across all stereogenic centres. It is equally important that, for a scaffold having a particular bond connectivity, all possible stereoisomers can be prepared. Thus a series of scaffolds of this type can be elaborated chemically into different but defined directions of 3-D space, to give isomeric compounds which may have very different properties in a chiral biological environment.

An important consideration in the development of synthetic routes towards scaffolds is that the chemistry should have the potential for scale-up. Then, in the event that the library screens generate useful lead compounds, the appropriate scaffold can be produced in sufficient quantity to support any subsequent drug discovery and development.

Pipecolic acid and 4-hydroxypipecolic acid are natural non-proteinogenic amino acids found in plants. In addition to the free amino acid, pipecolic acid is also found in complex biologically active molecules (for an example, see Nicolaou et al.; J. Am. Chem. Soc. 1993, 115, 4419–4420). Derivatives of pipecolic acid are known to display anaesthetic (GB-A-1166802), NMDA agonist and antagonist (Ornstein et al.; J. Med. Chem. 1989, 32, 827–833), anticoagulant (Okamoto et al.; Biochem. Biophys. Res. Commun. 1981, 101, 440446) and glycosidase activity (Bruce et al.; Tetrahedron 1992, 46, 10191–10200). Pipecolic acids have also been used in peptide chemistry as analogues of proline (Copeland et al.; Biochem. Biophys. Res. Commun. 1990, 169, 310–314). In the light of the diverse activities displayed by such pipecolic acid derivatives, single enantiomer libraries using such compounds as the scaffold would be a highly desirable tool for screening.

For a recent review of the synthesis of pipecolic acids, see Couty, Amino Acids 1999, 16, 297–320. A common synthetic route to racemic 4-hydroxypipecolic acid derivatives, has been to use an acyliminium ion cyclisation on a suitably protected homoallylic amine (Hays et al.; J. Org. Chem. 1990, 56, 4084–4086). This approach has been adapted to furnish enantiomerically pure cis 4-hydroxypipecolic acid derivatives provided a chiral protecting group is used in the synthesis (Beaulieu et al.; J. Org Chem. 1997, 62, 3440–3448). However, the protecting group does not offer any asymmetric induction, and the enantiomers have to be separated by a laborious co-crystallisation with (−)-camphorsulphonic acid. A similar approach to the synthesis reports a separation by recrystallisation of a diastereoisomeric intermediate (Skiles et al.; Bioorg. Med. Chem. Lett. 1996, 6, 963–966).

Another common theme in the synthesis of enantiomerically pure cis 4-hydroxypipecolic acid derivatives has been to fix the stereochemistry of the carboxylate group using a (L)-aspartic acid, and use this stereocentre to direct reduction of a ketone at the 4-position (Golubev et al.; Tetrahedron Lett. 1995, 36, 2037–2440; Bousquet et al.; Tetrahedron 1997, 46, 15671–15680). Two routes derived from carbohydrate starting materials have been reported, an atom inefficient synthesis starting from D-glucoheptono-1,4-lactone (Di Nardo and Varela; J. Org. Chem. 1999, 64, 6119–6125) and from D-glucosamine (Nin et al.; Tetrahedron 1993, 42, 9459–9464). All of these approaches yield only the cis-diastereoisomer. In particular, it remains a challenge to synthesise the two stereoisomers of trans-4-hydroxypipecolic acid in conveniently protected form, especially the N-Boc derivatives (i) and (ii)

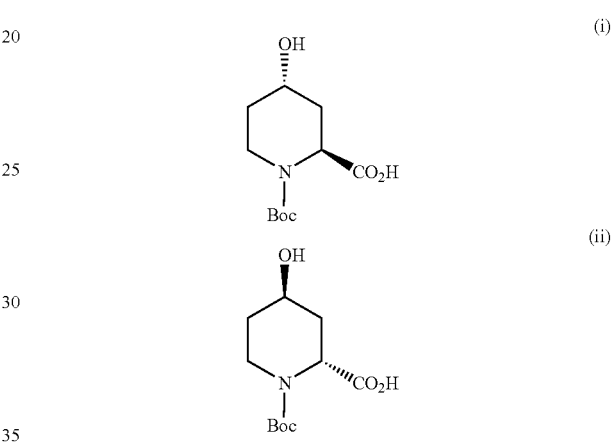

The most common approach has been to synthesise the cis-diastereoisomer, followed by a tedious inversion of the 4-hydroxy group. An alternative approach has utilised a ring expansion of 4-hydroxy-L-proline (Pellicciari et al.; Med. Chem. Res. 1992, 2, 491–496) and provides access to both diastereoisomers of 4-hydroxy-L-pipecolates. However, this route is unattractive on a large scale, owing to the two chromatographic steps needed for the separation of regio- and diastereomeric mixtures, and also the requirement for the hazardous reagent ethyl diazoacetate to effect ring expansion.

Both enantiomers of 2-acetamidopent-4-enoic acid are readily available in large quantities via bioresolution of a racemic mixture, and as such are valuable chiral building blocks. Using standard literature chemical methods, it is possible to convert both enantiomers of suitably protected 2-acetamidopent-4-enoic acid into mixtures of diastereoisomers (A) and (B)

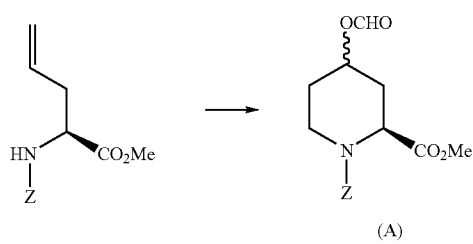

(A)

-continued

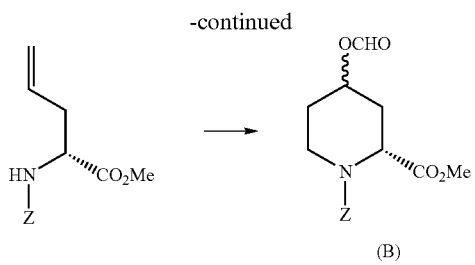

(B)

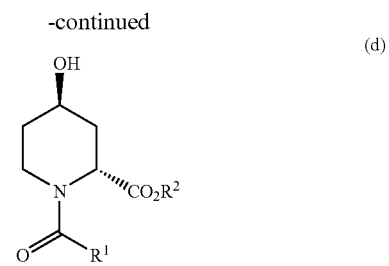

(d)

These diastereoisomeric ester mixtures (A) and (B) may be convenient intermediates for the preparation of scaffolds if their separation could be readily achieved. Although selective crystallisation can often provide a simple means to achieve scaleable separation of diastereoisomers, this technique is not applicable to mixtures (A) and (B), which are obtained as oils.

There are isolated reports in the literature that biocatalysis can be used as a means to effect separation of diastereoisomeric mixtures. For example, see Wang et al.; J. Org. Chem., 1998, 63, 4850–3; Hiroya et al.; Synthesis, 1995, 379–81; Mulzer et al.; Liebigs Ann. Chem., 1992, 1131–5.

SUMMARY OF THE INVENTION

One aspect of the present invention is based on a combination of realising the utility of a combination of complementary chiral scaffolds and of finding process chemistry that allows the preparation of such compounds on a commercial scale. For example, the present invention is based around novel process chemistry for the generation of a series of scaffolds comprising four trifunctionalised piperidines, the pipecolic acid derivatives (a)–(d)

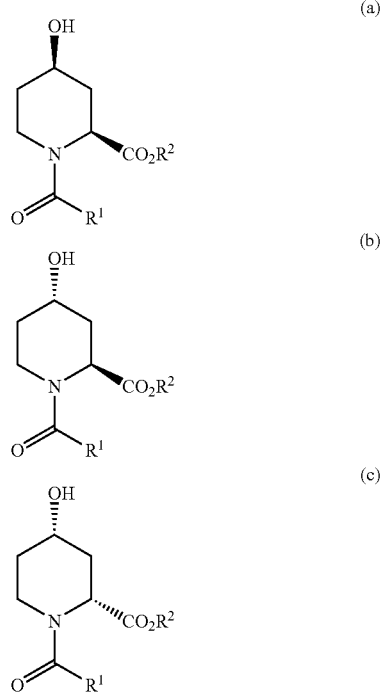

wherein $R^1$ is H, alkyl, alkoxy or aryl, and $R^2$ is H or alkyl. Such groups typically have up to 20 C atoms. In a preferred embodiment of the present invention, $R^1$ is benzyloxy and $R^2$ is methyl. For the purpose of this invention, $R^2$=H is understood to include salt forms.

The presence of N-Boc and methyl ester (or similar) protecting groups in these compounds allows selective elaboration of each of the functionalities present. Elaboration methods are well known to those skilled in the art.

For such further use, e.g. for the generation of libraries in combinatorial chemistry, the four chiral scaffolds (a–d) should be provided in a format where they can each be treated in the same manner, usually by the parallel, selective introduction of a group at one functionality on the ring, followed by deprotection of another functionality and the introduction of another group, etc. For this purpose, the scaffolds may be provided, in separate containers, in a single unit, e.g. a multi-well plate. From this arrangement, it is possible to generate a library of compounds comprising single enantiomers of respective compounds where structural distinction derives from the stereochemistry of ring substituents as shown by formulae (a)–(d).

In a particular aspect, the present invention is based on the discovery of biocatalytic separations of both of the diastereoisomeric mixtures (A) and (B), thus providing access to all four diastereoisomers of the piperidines without resorting to a chemical inversion step. The process described uses chemistry that is amenable to scale-up at each step.

Another aspect of the present invention is based on the discovery that novel salts of N-tert-butoxycarbamoyl-2S-carboxy-4S-hydroxypiperidine (i) and (ii), and the opposite enantiomers thereof, allow for the enhancement of diastereoisomeric excess (de) by recrystallisation/crystallisation of partially enriched material from a suitable solvent. Thus, while the corresponding free acid is an oil, the present invention provides, via simple cracking of enriched salts, a practical and scaleable method to access N-tert-butoxycarbamoyl-2S-carboxy-4S-hydroxypiperidine (i) or the opposite enantiomer thereof. This process offers a very high degree of purity control (chemical, diastereoisomeric and enantiomeric) over the products.

The novel salts may be represented by formula (1)

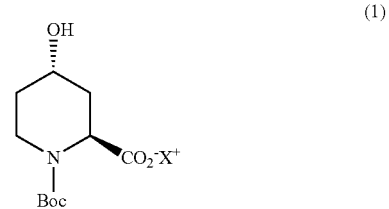

or the opposite enantiomer thereof, wherein $X^+$ is a cation.

DESCRIPTION OF PREFERRED EMBODIMENTS

By means of the invention, a piperidine of formula (4) in which the relative stereochemistry of C-2 and C-4 substituents is trans, may be conveniently prepared via the enzymic separation of the mixture of diastereoisomers represented by formula (5)

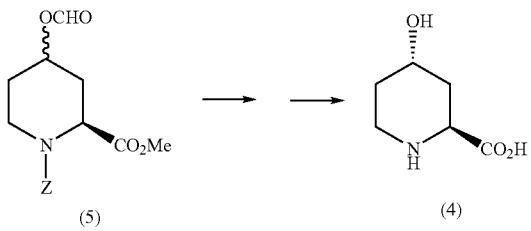

wherein Z is any suitable group.

The same approach is applicable to the opposite enantiomeric series. The resolution alone may not yield the piperidine (4) in sufficiently high diastereomeric purity. Thus, the corresponding N-Boc derivative (i), a conveniently protected form for further chemical elaboration, may be contaminated with the cis-diastereoisomer; the present invention provides means to separate these compounds.

An essential characteristic of novel salts (1) of the present invention is crystallinity. Suitable salts were identified by screening a range of amine bases, both achiral and chiral. Thus, in formula (1), $X^+$ represents a protonated amine, and X is typically a primary amine. Preferred primary amines are selected from the group comprising ethylamine, benzylamine and (S)-α-methylbenzylamine [(R)-α-methylbenzylamine for the opposite enantiomer]. Benzylamine is especially preferred.

The process of the present invention requires the salt (1) to be partially diastereomerically enriched prior to crystallisation/recrystallisation. Preferably, a salt of at least 60% de is used, more preferably of at least 80% de. Recrystallisation of such material leads to a significant enhancement of diastereomeric purity, typically to at least 90% de, and frequently to at least 95% de, or higher.

The identification of a solvent or a mixture of solvents suitable for recrystallisation of the salt (1) is carried out by conventional means, as would be practised routinely by a skilled practitioner. Such solvents are usually selected from $C_{1-4}$ alkanols, dialkyl ethers, and simple carboxylic esters such as ethyl acetate. In a preferred embodiment of the present invention, recrystallisation of the benzylamine salt of (1) from a 2:1 mixture of tert-butyl methyl ether and methanol effects an increase in diastereomeric purity from 80% de to >98% de.

The two pairs of diastereoisomers A and B can be resolved using an enzyme in a volume efficient manner; the substrate concentration is typically 100 g/L or higher. Suitable enzymes for the biocatalytic separation may be identified by conventional screening techniques. Although such screening may identify non-functional or less preferred enzymes, the general procedure is known and, as is routinely done, can be used to identify further functional enzymes. For the mixture of diastereoisomers A, the preferred enzyme is Lipase AY30. For the mixture of diastereoisomers B, the preferred enzyme is Chirazyme L9. Although both enzymes hydrolyse the trans-diastereoisomer preferentially, their modes of differentiating between cis and trans are clearly different. If each of the enzymes is used to hydrolyse the alternative diastereoisomeric pair, differences are clearly seen. Lipase AY30 preferentially hydrolyses the trans-diastereoisomer of Pair (B) whereas Chirazyme L9 does not hydrolyse either of Pair (A). Hence it can clearly be seen that in this case the selectivity of Lipase AY is governed by the relative stereochemistry at C-2 and C-4. This is a very unusual observation in enzymic resolutions, which normally differentiate stereocentres based on the absolute configuration of the site at which reaction occurs.

Scheme 1

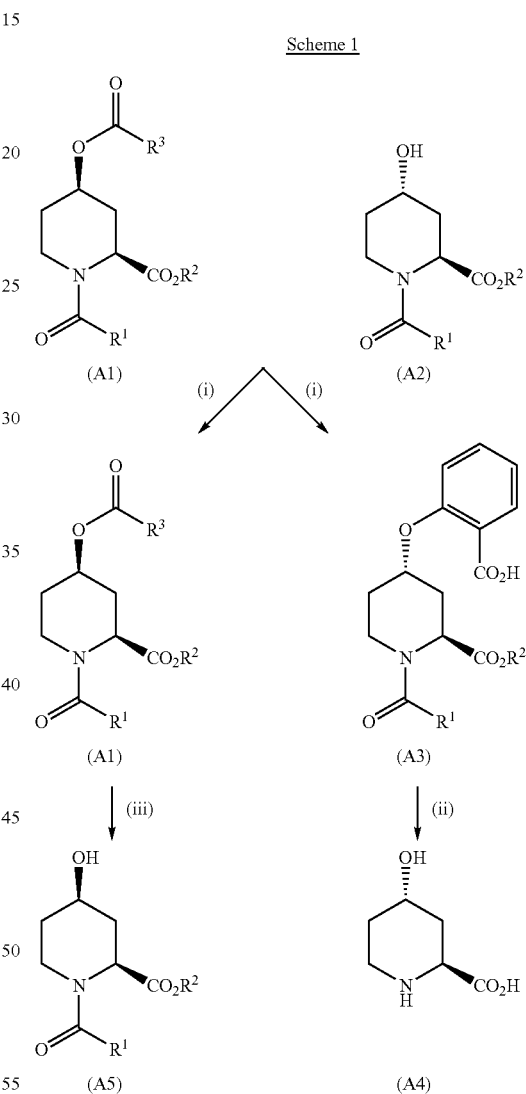

In Scheme 1, $R^3$ is H, alkyl or aryl, e.g. of up to 20 C atoms.

The products of the resolution are (A1) and (A2) from Pair (A), as shown in Scheme 1. (A1) and (A2) are inseparable, but reaction of the mixture with phthalic anhydride forms the hemiphthalate derivative (A3) from (A2), which can be separated from (A1) by partitioning between saturated aqueous ammonium carbonate and toluene (step (i)). (A3) is recovered from the aqueous phase by acidification to pH 1 and extraction into toluene and refluxing in 2M HCl (step (ii)) leaves the free amino acid (A4). The N-Boc derivative A4 can be subjected to the diastereoisomeric enrichment described above. In step (iii), (A1) is deformylated using standard conditions, typically potassium carbonate in methanol, to (A5), which, if $R^1$ is benzyloxy and $R^2$ is methyl, is a crystalline solid. Recrystallisation of this allows a control over the purity as well as a method to enhance the diastereomeric excess of this compound such that a single diastereoisomer compound can be obtained. Compounds (A5) and (A4) are easily converted to chiral scaffolds (a) and (b) respectively by conventional protecting group manipulations.

In a similar manner, products from the resolution of Pair (B) are the corresponding enantiomeric compounds (B1) and (B2) which can be elaborated using the same chemistry to scaffolds (c) and (d).

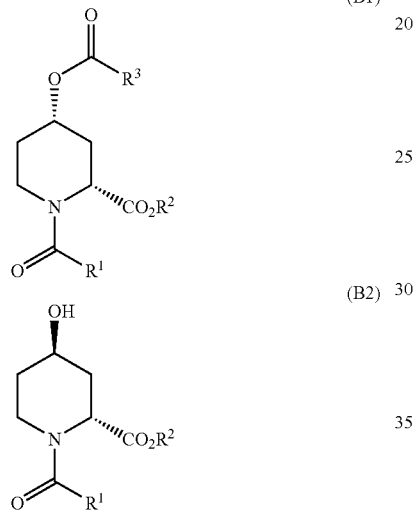

(B1)

(B2)

Overall, the process of the present invention provides a scaleable and operationally simple means of obtaining any one of the four chiral scaffolds (a)–(d) and congeners thereof.

The following Examples illustrate the invention. With regard to Example 4, see also Esch, et al; Tetrahedron 1991, 47, 4063–4076.

EXAMPLE 1

Synthesis of N-tert-butoxycarbamoyl-2R-carboxy-4R-hydroxypiperidine

To a solution of 2R-carboxy-4R-hydroxypiperidine (80% de, 140 g, 0.97 mol) in $H_2O$ (1 L) and THF (500 mL), $Et_3N$ (135 mL, 0.97 mol) was added dropwise. Di-tert-butyl dicarbonate (317 g, 1.46 mol) in THF (500 mL) was added in a steady stream. As the pH started to drop, a further portion of $Et_3N$ (135 mL, 0.97 mol) was added and the solution stirred at room temperature for 16 h. The THF was removed in vacuo and the resultant cloudy solution acidifed to pH 4 with 6M HCl and then to pH 3 with 1 M HCl. EtOAc was added and the mixture stirred for 2 min. The layers were separated, and the aqueous extracted with EtOAc (3×1 L). The combined organic extracts were washed with brine (1 L), dried ($MgSO_4$) and concentrated in vacuo to give N-tert-butoxycarbamoyl-2R-carboxy-4R-hydroxypiperidine as a viscous yellow oil (182 g, 76%). This material was used directly in the crystallisation described in Example 3.

Preparation of N-tert-butoxycarbamoyl-2S-carboxy-4S-hydroxypiperidine from 2S-carboxy-4S-hydroxypiperidine was carried out using the same method.

EXAMPLE 2

Crystallisation Screen: Amine Salts of N-tert-butoxycarbamoyl-2S-carboxy-4S-hydroxypiperidine Eight amines salts of N-tert-butoxycarbamoyl-2S-carboxy-4S-hydroxypiperidine were made using the following method: to a solution of 500 mg of 19% de N-tert-butoxycarbamoyl-2S-carboxy-4S-hydroxypiperidine in EtOAc (5 ml) at room temperature, a 1.1 molar equivalent of the amine was added. The solution was stirred at room temperature for 1 hr, then cooled in the fridge. Any crystals were harvested by filtration. The amines screened were ethylamine, octylamine, diisopropylamine, cyclohexylamine, dicyclohexylamine, benzylamine, R-α-methylbenzylamine and S-α-methylbenzylamine. The following amines gave crystalline salts: ethylamine, benzylamine and R-α-methylbenzylamine. The salts were recrystallised, and de values were determined by GC.

Ethylammonium salt: recrystallised from MeOH/EtOAc, de 70%

Benzylamine salt: recrystallised from MTBE, de 94%

R-α-methylbenzylammonium salt: recrystallised from MeOH/MTBE, de 98%

EXAMPLE 3

Preparation and Recrystallisation of N-tert-butoxycarbamoyl-2R-carboxy-4R-hydroxypiperidine, Benzylamine Salt N-tert-butoxycarbamoyl-2R-carboxy-4R-hydroxypiperidine (80% de, 182 g, 0.74 mol) was dissolved in EtOAc and the solution cooled on ice. Benzylamine (81.2 mL, 0.74 mol) was added dropwise and stirring maintained for 2 h. After overnight refrigeration, the solid was collected by filtration and dried. This solid (154 g) was recrystallised from MeOH (150 mL) and MTBE (300 mL). Filtration yielded N-tert-butoxycarbamoyl-2R-carboxy-4R-hydroxypiperidine, benzylamine salt of de >98% as a white solid (104 g, 40%).

$^1$H NMR (400 MHz, $CD_3OD$) 7.40 (5H, m) 4.67 (0.4 H, minor rotamer, m) 4.59 (0.6H, d, J 5.5, major rotamer) 4.10 (2H, s) 3.94 (1H, br d, J 13.0) 3.59 (1H, m) 3.17 (1H, m) 2.48 (1H, m) 1.80 (1H, m) 1.43 (10H, m) 1.25 (1H, m).

Preparation and recrystallisation of N-tert-butoxycarbamoyl-2S-carboxy-4S-hydroxypiperidine, benzylamine salt was carried out using the same method.

EXAMPLE 4

Preparation of N-benzyloxycarbamoyl-2S-carbomethoxy-4R,S-formyloxypiperidine(methyl(N-benzyloxycarbamoyl)-4-formyloxypipecolate)

Paraformaldehyde (144.0 g, 4.8 mol) was dissolved in hot formic acid (6.5L) and the resultant solution cooled to 25° C. Methyl (2S-benzyloxycarbamoyl)-pent-4-enoate (904.3 g, 3.4 mol) was added and the solution stirred for 72 hrs, at which time GC analysis showed no starting material remained. Excess solvent was removed in vacuo, and the residual oil dried by azeotroping with toluene (4×750 mL)

and passed through a silica plug, eluting with EtOAc. Evaporation of the solvent in vacuo left N-benzyloxycarbamoyl-2S-carbomethoxy-4R,S-formyloxypiperidine as a yellow oil (1056.3 g, 96%), of diastereomeric ratio 1:1.

GC gave: retention time 26.9 min (trans diastereoisomer) 27.6 min (cis diastereoisomer)

Synthesis of N-benzyloxycarbamoyl-2R-carbomethoxy-4R,S-formyloxypiperidine was carried out from methyl (2R-benzyloxycarbamoyl)-pent-4-enoate using the same method and resulted in an equivalent set of products.

EXAMPLE 5

Enzymic Hydrolysis Screen of N-benzyloxycarbamoyl-2S-carbomethoxy-4R,S-formyloxypiperidine (Mixture A)

Eight enzymes were screened to evaluate their potential for hydrolysing either the R- or S-formate ester. The enzymes used were Chirazyme L1, Chirazyme L2, Chirazyme L9, Lipase PS, Lipase AY30, Lipase A6, Porcine Pancreatic Lipase and *Rhizopus javanicus* Lipase. In each case, 150 mg of substrate was placed in a scintillation vial with 1.5 mL of 50 mM potassium phosphate buffer pH 7.0, 1.5 mL MTBE and 10 mg of enzyme. The reactions were continuously agitated at 25° C. in a water bath/shaker. After 24 hr, tlc analysis showed Chirazyme L1 and Lipase AY30 selectively hydrolysed the substrate. GC analysis of these two reactions indicated that Lipase AY30 was the more selective enzyme, preferentially hydrolysing the trans-diastereoisomer, and that Chirazyme L1 showed an opposite selectivity, towards cis-diastereoisomer.

A similar screen was carried out on the substrate N-benzyloxycarbamoyl-2R-carbomethoxy-4R,S-formyloxypiperidine (mixture B) using the same eight enzymes. In this case, Lipase AY30 and Chirazyme L9 were the only enzymes to selectively hydrolyse the substrate. Both demonstrated the same selectivity, preferentially hydrolysing the trans-diastereoisomer, with Chirazyme L9 the more selective.

EXAMPLE 6

Enzymic Resolution of N-benzyloxycarbamoyl-2S-carbomethoxy-4R,S-formyloxypiperidine A 10 L jacketed reaction vessel equipped with an overhead stirrer was charged with N-benzyloxycarbamoyl-2S-carbomethoxy-4R,S-formyloxypiperidine (1056.3 g), MTBE (3.6 L) and 50 mM potassium phosphate buffer pH 7.0 (4.5 L). Stirring was started to achieve an emulsion, the pH adjusted back to 7.0 with 5M NaOH and the temperature set to 20° C. Lipase AY30 (300 g) was added and stirring continued at 20° C. At all times in the reaction, the pH was kept constant at pH 7.0 by the addition of 5M NaOH. After 4 days at 20° C., the reaction was stopped by filtration through Celite 521. The two layers in the filtrate were separated, and the organic layer reserved. The Celite was slurried with acetone (500 mL) and filtered. This filtrate was concentrated in vacuo until only aqueous material remained, when it was extracted with MTBE (2×500 mL). The organic layers were combined, dried (MgSO$_4$) and concentrated in vacuo to yield a viscous, cloudy yellow oil (903 g) that was a mixture of the residual starting material, N-benzyloxycarbamoyl-2S-carbomethoxy-4R-formyloxypiperidine, of 83% de, and product, N-benzyloxycarbamoyl-2S-carbomethoxy-4S-hydroxypiperidine, of 90% de in an approximate 1:1 ratio. This oil was used immediately in the next step.

EXAMPLE 7

Separation of the Mixture of Compounds Obtained from the Enzymic Resolution

The mixture obtained in Example 6 (900 g) and DMAP (17.9 g, 0.14 mol) was dissolved in CH$_2$Cl$_2$ (6 L) at 20° C. Et$_3$N (450 mL, 3.22 mol) was added using a pressure equalising dropping funnel over a 10 minute period. Solid phthalic anhydride (239 g, 1.61 mol) was added batch-wise and stirring continued for 18 hr. The reaction mixture was washed with 1 M HCl (3.5 L), and the organic layer concentrated in vacuo. The residue was redissolved in toluene (4 L) and extracted with saturated (NH$_4$)$_2$CO$_3$ (3 L). This aqueous layer was washed with toluene (1 L), and the combined organic extracts dried (MgSO$_4$) and concentrated in vacuo to yield N-benzyloxycarbamoyl-2S-carbomethoxy-4R-formyloxypiperidine (545 g, 81% d.e., 52% yield overall from Example 3). The aqueous layer was acidified to pH 1 with conc. HCl and extracted with toluene (2 L). The layers were separated, and the aqueous extracted once more with toluene (1 L). These two organic layers were combined, dried (MgSO$_4$) and concentrated in vacuo to yield N-benzyloxycarbamoyl-2S-carbomethoxy-4S-hydroxypiperidine, 4-hemiphthalate derivative (553 g, 38% yield overall from Example 6). Both products were used directly in the next steps.

Using the same methods as outlined in Examples 6 and 7, N-benzyloxycarbamoyl-2R-carbomethoxy-4R,S-formyloxypiperidine was separated into N-benzyloxycarbamoyl-2R-carbomethoxy-4S-formyloxypiperidine and N-benzyloxycarbamoyl-2R-carbomethoxy-4R-hydroxypiperidine, 4-hemiphthalate derivative, the only difference being the use of Chirazyme L9 in place of Lipase AY30 in the enzymic resolution.

EXAMPLE 8

Preparation of N-benzyloxycarbamoyl-2S-carbomethoxy-4R-hydroxypiperidine

81% de N-Benzyloxycarbamoyl-2S-carbomethoxy-4R-formyloxypiperidine (545 g, 1.70 mol) was dissolved in MeOH (1.5 L) and K$_2$CO$_3$ (23.5 g, 0.17 mol) added. The mixture was stirred for 2 hr at room temperature, by which time the reaction was complete. MTBE (5 L) was added and the solution washed with H$_2$O (3 L). The organic phase was dried and concentrated in vacuo. The residue was dissolved in hot EtOAc (600 mL), cooled and crystallisation induced by the addition of heptane (75 mL). The crystals obtained were filtered and recrystallised from EtOAc (850 mL) to yield N-benzyloxycarbamoyl-2S-carbomethoxy-4R-hydroxypiperidine (145.4 g, >99% d.e.). A further crop of identical quality crystals (58.2 g, >99% d.e.) were obtained from the liquors (overall yield 41%).

$^1$H NMR (400 MHz, d$_6$-DMSO) 7.37 (5H, m) 5.08, 2H, m) 4.64 (2H, m) 3.90 (1H, br s) 3.70 (1H, dt, J 8.5, 3.5) 3.59 (3H, br s) 3.47–3.27 (1H, br m) 2.19 (1H, m) 1.82 (1H, dd, J 13.5, 6.5) 1.54 (2H, m). GC (material derived to acetate) gave retention times 28.2 (minor diastereoisomer), 29.0 (major diastereoisomer) in a ratio 1:220.

Synthesis of N-benzyloxycarbamoyl-2R-carbomethoxy-4S-hydroxypiperidine was carried using the same method and resulted in an equivalent product. An X-ray structure was used to confirm the stereochemistry of this compound.

EXAMPLE 9

Preparation of 2S-carboxy-4S-hydroxypiperidine

N-benzyloxycarbamoyl-2S-carbomethoxy-4S-hydroxypiperidine 4-hemiphthalate (365 g, 0.82 mol) was mixed with 2M HCl (1.5 L) and heated to reflux for 5 days. The mixture was cooled and extracted with EtOAc (3×1 L). The aqueous layer was concentrated in vacuo to leave a cloudy paste (170 g). This was redissolved in $H_2O$ (500 mL) and the solution neutralised using Amberlite IRA-93. The resin was filtered and washed with $H_2O$ (1.5 L). The filtrate was concentrated in vacuo and dried by azeotroping with toluene (2×500 mL) to leave a cream solid (94.5 g, 79%, 88% de).

$^1$H NMR (400 MHz, $D_2O$) major diastereoisomer 4.21 (1H, m) 3.90 (1H, dd, J 11.5, 3.5) 3.28 (2H, m) 2.20 (1H, m) 1.97–1.84 (3H, m). Minor diastereoisomer 3.95 (1H, m) 3.63.(1H, dd, J 13.0, 3.0) 3.47 (1H, ddd, J 13.0, 4.5, 2.5)3.02 (1H, dt, J 13.5, 3.5)2.47 (1H, m) 2.10 (1H, m), 1.58 (2H, m).

Synthesis of 2R-carboxy-4R-hydroxypiperidine was carried using the same method and resulted in an equivalent product.

The invention claimed is:

1. A crystalline salt according to formula (1) or the opposite enantiomer thereof, wherein $X^+$ is a cation.

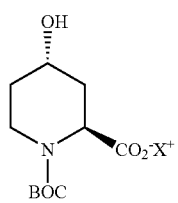

(1)

2. A salt according to claim 1; wherein $X^+$ is a protonated amine.

3. A salt according to claim 2, wherein the amine is a primary amine.

4. A salt according to claim 3, wherein the primary amine is benzylamine.

5. A salt according to claim 3, wherein the primary amine is ethylamine.

6. A salt according to claim 2, wherein the amine is a chiral primary amine.

7. A salt according to claim 6, wherein the chiral primary amine is (S)-or (R)-α-methylbenzylamine.

8. A salt according to any preceding claim, which is diastereomerically enriched.

9. A salt according to claim 8, of at least 60% diastereomeric excess (% de).

10. A salt according to claim 9, of at least 80% diastereomeric excess (% de).

11. A salt according to claim 10, of at least 95% diastereomeric excess (% de).

12. A process for enhancing the diastereoisomeric purity of the crystalline salt of any preceding claim, which comprises crystallization or recrystallisation.

13. A process for the preparation of an enantiomerically enriched trans- 1,4 disubstituted pipecolate derivative of formula (2), substantially free of the corresponding cis-isomer, which comprises selective hydrolysis of a mixture of diastereoisomeric esters (3a) and (3b) wherein $R^1$ is H, alkyl, alkoxy or aryl, $R^2$ is H or alkyl, and $R^3$ is H, alkyl or aryl, in the presence of a hydrolytic enzyme, and wherein a mixture of the opposite enantiomers of (3a) and (3b) may alternatively be used in order to prepare the opposite enantiomer of (2) as product.

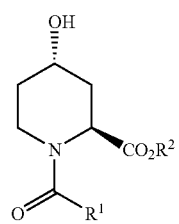

(2)

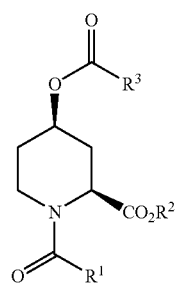

(3a)

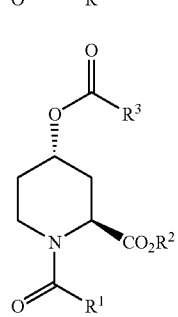

(3b)

14. A process for the preparation of an enantiomerically enriched cis-1,4disubstituted pipecolate derivative of formula (3a) as depicted in claim 13, substantially free of the corresponding trans-isomer (3b), which comprises selective hydrolysis of (3b) Present in a mixture of (3a) and (3b), forming deacylated trans-isomer (2), wherein $R^1$ is H, alkyl, alkoxy or aryl, $R^2$ is H or alkyl, and $R^3$ is H, alkyl or aryl, in the presence of a hydrolytic enzyme, and wherein a mixture of the opposite enantiomers of (3a) and (3b) may alternatively be used in order to prepare the opposite enantiomer of(3a).

15. A process according to claim 14, wherein the enzyme is AY30 lipase, for the preparation of a compound of formula (3a).

16. A process according to claim 14, wherein the enzyme is Chirazyme L9, for the preparation of a compound of formula (3a) wherein the absolute configuration is opposite to that depicted in claim 13.

17. A process according to claim 13 or 14, wherein $R^3$ is H.

18. A process according to claim 13, 14, or 17 wherein $R^2$ is H or a salt form thereof or alkyl, preferably methyl.

19. A process according to claim 13, 14, 17, or 18 wherein R' is alkoxy, preferably benzyloxy or t-butyloxy.

20. A process according to claim 13, wherein the enzyme is AY30 lipase, for the preparation of a compound of formula (2).

21. A process according to claim 13, wherein the enzyme is Chirazyme L9 for the preparation of a compound of formula (2).

22. A process according to claim 13, which further comprises 0-acylation of compound (2), to form a hemiphthalate ester.

23. A process according to claim 22, wherein compound (2) is in admixture with compound (3a), and the hemiphthalate ester is separated therefrom by partitioning the mixture between an aqueous base and an immiscible organic solvent.

24. A process according to any of claims 13 and 14–23, for the preparation of the compounds of formulae (a), (b), (c) and (d)

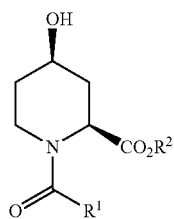
(a)

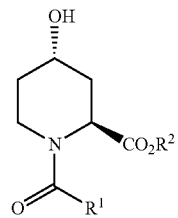
(b)

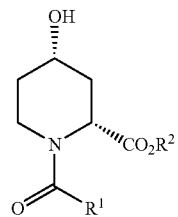
(c)

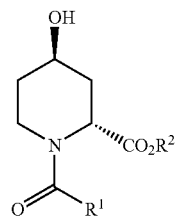
(d)

* * * * *